United States Patent [19]

Layman, Jr. et al.

[11] Patent Number: 5,777,169

[45] Date of Patent: Jul. 7, 1998

[54] PRODUCTION OF HIGH PURITY ALKALI METAL DIARYLPHOSPHIDE AND CYCLOALKYLDIARYLPHOSPHINES

[75] Inventors: William J. Layman, Jr.; George W. Welsh. both of Orangeburg. S.C.

[73] Assignee: Albemarle Corporation. Richmond. Va.

[21] Appl. No.: 886,629

[22] Filed: Jul. 1, 1997

[51] Int. Cl.$^6$ .................................................. C07F 9/50
[52] U.S. Cl. ................................................... 568/17
[58] Field of Search ........................................... 568/17

[56] References Cited

U.S. PATENT DOCUMENTS

| | | | |
|---|---|---|---|
| 4,618,720 | 10/1986 | Bay | 568/17 |
| 5,288,912 | 2/1994 | Devon | 568/17 |
| 5,654,485 | 8/1997 | Senaratne | 568/17 |

OTHER PUBLICATIONS

Aguiar et al., "Lithium Diphenylphosphide: A Convenient Source and Some Reactions", JOC Mar. 1962, vol. 27, pp. 1001–1004.

Toth et al., "Aspects of the Cleavage of Phosphines with Potassium: Synthesis and Reactivity of Lithium and Potassium Bis(p-(dimethylamino)phenyl)phosphide", Organometallics 1990, vol. 9, No. 3, pp. 675–680.

Rossi et al., "Reaction of 1-Bromoadamantane with Diphenylphosphide and Dipenylarsenide Ions by the SRN1 Mechanism. Facile Nucleotphilic Substitution at the Bridgehead Position", J Org Chem 1982, vol. 47, No. 24, pp. 4654–4657.

Aguiar et al., "The Reaction of Lithium Diphenylphosphide and Simple Aryl Halides", Aug. 1963, vol. 28, pp. 2091–2093.

Tsvetkov et al., "A Simple Synthesis and Some Synthetic Applications of Substituted Phosphide and Phosphinite Anions", Synthesis, Mar. 1986, pp. 198–208.

Hayashi et al., "Catalytic Asymmetric Hydroformylation by the Use of Rhodiumcomplexes of Chiral Bidentate Phosphorus Ligands Bearing Saturated Ring Skeletons", Sep. 1979, Bulletin of the Chemical Society of Japan, vol. 52, No. 9, pp. 2605–2608.

Morrison et al., "Synthesis of Menthyl-and Neomenthyl-diphenylphosphine. Epimeric, Chiral, Tertiary Phosphine Ligands for Asymmetric Synthesis", J Org Chem, vol. 39, No. 2, 1974, pp. 270–272.

Wittenberg and Gilman, "Lithium Cleavages of Triphenyl Derivatives of Some Group Vb Elements in Tetrahydrofuran", J Org Chem vol. 23, pp. 1063–1065, Jul. 1958.

Kuchen and Buchwald, "Reactions of diphenylphosophine Sodium", Angew Chem 69, pp. 307–308 (1957)–Abstract Attached.

Primary Examiner—Gary Geist
Assistant Examiner—Jean F. Vollano
Attorney, Agent, or Firm—Philip M. Pippenger

[57] ABSTRACT

(1) Alkali metal diarylphosphides are formed by mixing triarylphosphine with, and preferably introducing triarylphosphine into, a two-phase mixture one or more alkali metals, preferably a mixture or alloy of sodium and potassium, in an anhydrous organic liquid diluent in the presence of molecular hydrogen. (2) To form a cycloalkyldiarylphosphine, at least a portion of the reaction mixture formed as in (1) (or alkali metal diarylphosphide recovered therefrom) and cycloalkyl mesylate or tosylate are mixed together and maintained under suitable reaction conditions. Reaction (2) is driven by the presence of residual sodium from reaction (1). Conduct of reaction (2) under a hydrogen atmosphere suppresses undesirable side reactions.

25 Claims, No Drawings

PRODUCTION OF HIGH PURITY ALKALI METAL DIARYLPHOSPHIDE AND CYCLOALKYLDIARYLPHOSPHINES

BACKGROUND

Alkali metal diarylphosphides are useful as raw materials for the production of cycloalkyldiarylphosphines such as neomenthyldiphenylphosphine and menthyldiphenylphosphine. Such phosphines are examples of ligands which impart to transition metal complexes the potential for diastereomeric interactions with unsaturated organic substrates, thus making asymmetric synthesis possible. Note in this connection, J. D. Morrison and W. F. Masler, *J. Org. Chem.*, 1974, Vol. 39, No. 2, pages 270–272. Neomenthyldiphenylphosphine is of particular importance for the preparation of noble metal catalysts useful in the synthesis of certain pharmaceuticals such as naproxen, ketoprofen, ibuprofen, etc.

Heretofore, sodium diphenylphosphide has been produced by reacting triphenylphosphine with about 4 equivalents of sodium. The yield of such reaction has been less than about 57%. It is also known that 2 equivalents of alkali metal dissolved in liquid ammonia can reduce triphenylphosphine to alkali metal diphenylphosphide. Reactions with liquid ammonia require special conditions and equipment, and are not desirable for commercial operations.

Because of the shortcomings inherent in these previously-known processes, a need has existed for a commercially feasible process capable of producing alkali metal diarylphosphides of high purity in high yields. This invention is deemed to fulfill this need most expeditiously.

THE INVENTION

It has been found that by mixing together a triarylphosphine and a dispersion of alkali metal, most preferably a sodium-potassium alloy, in a suitable liquid medium and in the presence of molecular hydrogen, improved yields of alkali metal diarylphosphide can be achieved.

Thus this invention provides in one of its embodiments a process of preparing at least one alkali metal diarylphosphide which comprises mixing together (1) at least one triarylphosphine optionally, but preferably, dissolved in an anhydrous organic liquid diluent, and (2) a two-phase mixture (e.g., a slurry or a dispersion) of at least one alkali metal in an anhydrous organic liquid diluent, in the presence of molecular hydrogen and under conditions effective to produce at least one alkali metal diarylphosphide. Any mode of accomplishing such mixing of (1) and (2) together can be used, such as addition of (1) to (2) and/or addition of (2) to (1), and/or concurrent feeding of (1) and (2) to the reaction vessel. However especially good results are achieved when (1) is introduced into (2).

In particular, it has been found that by feeding the triarylphosphine to the dispersion of alkali metal, most preferably a sodium-potassium alloy, in a suitable liquid medium and in the presence of molecular hydrogen, nearly quantitative production of high purity alkali metal diarylphosphide can be achieved.

Thus this invention provides in one of its preferred embodiments a process of preparing at least one alkali metal diarylphosphide which comprises introducing at least one triarylphosphine into a two-phase mixture (e.g., a slurry or a dispersion) of at least one alkali metal in an anhydrous organic liquid diluent in the presence of molecular hydrogen and under conditions effective to produce at least one alkali metal diarylphosphide. The triarylphosphine can be added in neat form, but preferably is added to the two-phase mixture as a solution in an anhydrous solvent. Preferably, the solvent for the triarylphosphine is the same organic liquid as the diluent for the two-phase mixture as this simplifies processing and is a highly cost-effective way of operating.

A significant advantage of the above preferred process is that when it is properly performed, all or a portion of the reaction product can be used, without workup, in the synthesis of cycloalkyldiarylphosphide ligands such as a neomenthyldiarylphosphide. This is made possible because of the high yields and purities of the alkali metal diarylphosphides that are achieved when the above-described process is carried out in the proper manner.

Accordingly, another embodiment of this invention is a process for the preparation of a cycloalkyldiarylphosphine which comprises:

a) introducing at least one triarylphosphine into a two-phase mixture (e.g., a slurry or a dispersion) of at least one alkali metal in an anhydrous organic liquid diluent in the presence of molecular hydrogen and under conditions effective to produce at least one alkali metal diarylphosphide such that a reaction mixture containing at least one alkali metal diarylphosphide is formed; and b) mixing together (i) at least a portion of the reaction mixture of a), and (ii) at least one cycloalkyl mesylate or tosylate under conditions effective to form at least one cycloalkyldiarylphosphine.

It is preferred conduct step a) such that the conversion of the triarylphosphine reactant is substantially complete (e.g., at least about 95% converted), and then to add the cycloalkyl mesylate or tosylate to the reaction mixture of a). This enables the reactions to be performed as "one-pot", high yield reactions with no product workup between the two reactions, features which are highly desirable in commercial plant operations.

Synthesis of Alkali Metal Diarylphosphide

As noted above, one triarylphosphine or a combination of triarylphosphines is mixed with, and preferably introduced into, a two-phase mixture (e.g., a slurry or a dispersion) of at least one alkali metal in an anhydrous organic liquid diluent in the presence of molecular hydrogen. The reaction mixture preferably contains a sufficient amount of the anhydrous organic liquid diluent (and solvent for the triarylphosphine, if such solvent is used) so that the alkali metal diarylphosphide is formed in solution. Most preferably, there is a sufficient amount of such liquid diluent (and solvent, if used) such that the alkali metal diarylphosphide is formed and remains in solution at all times.

The hydrogen can be introduced into the reaction vessel before or concurrently with, or subsequent to, the introduction of (1) and/or (2) above as long as the hydrogen is present during a substantial portion of the reaction period (e.g., at least 75% of the period during which (1) and (2) are undergoing reaction with each other. Preferably the triarylphosphine is introduced into the reaction vessel that already contains the above two-phase mixture under an atmosphere of hydrogen. It is desirable to suitably stir, shake or otherwise agitate the reaction mixture to ensure intimate contact of the reactants with each other.

Any of a variety of triarylphosphines can be used in the process. The aryl groups can be the same or different from each other, and typically they each will contain up to about 18 carbon atoms. Preferred triarylphosphines are those in which each aryl group contains 6 to 10 carbon atoms and has only aromatic unsaturation. Examples include triphenylphosphine, tritolylphosphine (o-, m-, or p-tolyl isomer, or mixture of any two or of all three such isomers), bis(phenyl)-o-tolylphosphine, phenylbis(p-tolyl)phosphine, tri(xylyl)phosphine (mixed xylyl isomers), bis(phenyl)-p-ethylphenylphosphine, 2-naphthyl-bis(phenyl)phosphine, trinaphthylphosphine, tetrahydronaphthylbis-o-tolylphosphine, and the like.

Solvents which preferably are used in forming a solution of the triarylphosphine include one or more paraffinic, cycloparaffinic and/or aromatic hydrocarbons; one or more cyclic and/or acyclic, mono- and/or polyethers; one or more tertiary amines; a mixture of one or more of such hydrocarbons and one or more of such ethers, a mixture of one or more of such hydrocarbons and one or more of such tertiary amines, a mixture of one or more of such ethers and one or more such tertiary amines, and a mixture of one or more of such hydrocarbons, one or more of such ethers, and one or more of such tertiary amines. The solvents should be materials that are in the liquid state at ambient room temperature and pressure conditions and preferably that remain in the liquid state under the temperature and pressure conditions used in the reaction in which the alkali metal diarylphosphide is formed. Illustrative solvents include, hexane, heptane, octane, nonane, decane, cyclohexane, methylcyclohexane, toluene, xylene, ethylbenzene, tetrahydronaphthalene, tetrahydrofuran, one or more methyltetrahydrofuran isomers, p-dioxane, dimethoxyethane, diglyme, methyl-tert-butyl ether, methyl-tert-amyl ether, ethyl-tert-butyl ether, diethyl ether, tetrahydrofurfuryl ethyl ether, tetrahydrofurfuryl n-butyl ether, triethylamine, tributylamine, triisoamylamine, pyridine, quinoline, N-methylmorpholine, and similar materials, including mixtures of the foregoing. Particularly preferred are tetrahydrofuran and alkyl-substituted tetrahydrofurans.

While any alkali metal or mixture of alkali metals can be used, potassium is preferred as its reaction rate is much faster than that of sodium, and thus is the most cost-effective alkali metal for use in the practice of this invention. Alloys or mixtures of sodium and potassium are most preferred. Excellent results have been achieved to date using a sodium-potassium alloy having the empirical formula $NaK_2$.

The diluent for the alkali metal can be one or more liquid hydrocarbons and/or one or more liquid ethers and/or one or more tertiary amines, or mixtures of any two or all three such diluent types. As noted above, when a solvent is used with the triarylphosphine, the diluent for the alkali metal(s) is preferably, but not necessarily, the same substance.

If the alkali metal diarylphosphide is being synthesized for purposes other than carrying out a process of this invention in which step b) above is also to be performed, the proportions of the alkali metal to the triarylphosphine are not of particular significance as the stoichiometry of the reaction involves one mole of alkali metal per mole of triarylphosphine, and thus the reactant present in a lesser proportion becomes the limiting reactant. Usually in such cases, the proportions of alkali metal to triarylphosphine will be in the range of about 0.5 to about 3 moles of alkali metal per mole of triarylphosphine, and preferably in the range of about 0.8 to about 1.2 moles of alkali metal per mole of triarylphosphine.

The situation is quite different when carrying out the embodiment of this invention involving both of steps a) and b) above. In this case proportions of potassium, whether used individually or as a component of an alloy or mixture with sodium, in the range of about 0.8 to about 1.0 mole of potassium per mole of triarylphosphine are typical. A lower proportion of potassium can be used but since it is the limiting reactant in such cases, it is not a preferred mode of operation. Preferably the proportion of potassium, whether used individually or as a component of an alloy or mixture with sodium, is in the range of about 0.95 to about 1.0 mole per mole of triarylphosphine. Unreacted potassium undergoes undesirable reactions in step b), and unreacted rubidium and/or cesium would be expected to undergo similar undesirable reactions in step b), thereby reducing yields of the cycloalkyldiarylphosphine end product of the two-step process. Thus to achieve optimum yields approaching quantitative yields in step b), it is desirable to ensure that the amount of metallic K (and/or Rb and/or Cs if present) used in step a) does not appreciably exceed one mole per mole of the triarylphosphine reactant being used. If rubidium or cesium is used the proportions thereof would be similar to that of potassium. On the other hand, sodium reacts with the triarylphosphine much more slowly than potassium, so much so that the presence of the sodium in a sodium-potassium alloy in most cases can be ignored in calculating the proportions of such alloy to be used in reaction with the triarylphosphine. The presence of the sodium is, however, highly beneficial in that on completion of the reaction between an alloy such as NaK or $NaK_2$ and triarylphosphine, the residual unreacted sodium drives and accelerates step b), i.e., the subsequent reaction with the mesylate or tosylate. Lithium is less preferred than potassium in view of the higher cost and anticipated lower reaction rate of lithium in the process as compared to potassium.

The reaction between the triarylphosphine(s) and alkali metal(s) is typically performed at under a pressurized atmosphere of hydrogen at one or more temperatures in the range of about −10° to about 110° C. Preferred temperatures are in the range of about 25° to about 45° C. Hydrogen pressures are typically in the range of about 3 to about 1000 psig, and preferably are in the range of about 10 to about 50 psig. Reaction periods are typically in the range of about 1 hour to about 48 hours, and in general, are inversely proportional to the temperature(s) and pressure(s) employed. If desired, the hydrogen atmosphere can be diluted with an inert gas, such as nitrogen, argon, helium, neon, krypton, etc.

Since alkali metals are involved in the reaction, the reaction environment should, of course, be essentially anhydrous and essentially free of air and molecular oxygen.

Synthesis of Cycloalkyldiarylphosphine

In this embodiment of the invention, all or a portion of the reaction mixture of step a) above is mixed with one or more cycloalkyl mesylates or tosylates and the mixture is maintained and/or subjected to reaction conditions effective to form at least one cycloalkyldiarylphosphine.

Highly useful mesylates and tosylates are monoalkyl- or polyalkyl-substituted cycloalkyl mesylates or tosylates in which an alkyl group is in the 2-position. Such mesylate or tosylate preferably has from 5 to 8 carbon atoms in the ring and has a linear or branched alkyl group of up to about 12 carbon atoms substituted on one of the ortho positions of the cycloalkyl ring relative to the mesylate or tosylate functionality. In addition the cycloalkyl ring may contain other substituents which are innocuous in the sense that they will not impair or inhibit the desired reaction. While such additional substituents can be in any positions which do not unduly sterically hinder the mesylate or tosylate functional group, such substituents are preferably in the meta or para positions relative to the mesylate or tosylate functional group. Examples of such innocuous substituents include alkyl groups, alkenyl groups, hydrocarbyloxy groups, hydrocarbylthio groups, hydrocarbylcarbonyl groups, hydrocarbyloxyhydrocarbyl groups, and heteroaromatic groups, dihydrocarbyl-amino groups, and combinations of two or more of these. Typically this reactant will contain a total of up to about 24 carbon atoms, and preferably up to about 18 carbon atoms, in the molecule. As regards cycloalkyl ring size, most preferably the ring is a 6-membered ring. The ortho-alkyl substituent is preferably a secondary alkyl group, which most preferably contains up to about 6 carbon atoms. Particularly preferred reactants are menthyl mesylate and menthyl tosylate.

Usually step b) is performed at one or more temperatures in the range of about 20° to about 100° C. A preferred range is from about 25° to about 55° C. The reaction is preferably performed at atmospheric pressure, although this is not essential. For example, if using a solvent that has a boiling point below the reaction temperature selected for use in the process, the reaction should be performed under superatmospheric pressure sufficient to keep the solvent in the liquid state. Likewise reduced pressure can be employed under suitable circumstances (e.g., use of a high boiling reaction medium, etc.). Proportions are not critical, but normally will be relatively close to equimolar, e.g., from about 1 to about 1.2 moles of the cycloalkyl mesylate or tosylate per mole of the alkali metal diarylphosphide. The reaction should be conducted under a dry inert atmosphere.

Particularly preferred reaction conditions, especially when causing reaction of neomenthyl mesylate with reaction mixture from step a) wherein a sodium-potassium alloy had been used, involve temperatures in the range of about 35° to about 55° C. Reaction at about 25° C. proceeds cleanly in 24 hours. At temperatures of about 35° C., the reaction tends to take off exothermically, and proceeds nicely at about 38° to about 55° C. As pointed out above, the presence of residual sodium (or sodium hydride formed in situ) in the reaction mixture from step a) drives the reaction of step b) and makes possible the achievement of almost quantitative yields of the cycloalkyldiarylphosphine, such as neomenthyldiphenylphosphine. Without being bound by theoretical considerations, it is believed that the residual sodium or sodium hydride present in step b) reacts with diarylphosphine formed in the reaction mixture to regenerate diarylphosphide anion, and thus drives the conversion of diaryl phosphine to near 100%. It further appears that at least some cycloalkyldiarylphosphines such as neomenthyldiphenylphosphine will react very slowly with sodium to yield reduction products such as diarylphosphide and neomenthylmonoarylphosphide anions as well as aryl and menthyl radicals. To suppress these undesirable side reactions, it is preferable, though not essential, to conduct step b) under a hydrogen atmosphere.

The mesylate or tosylate is preferably employed as a preformed solution in a suitable solvent, which most preferably is the same substance as that used as the diluent for the two-phase mixture in step a).

It should be noted that lithium diarylphosphides tend to interact with ethers, especially cyclic ethers such as tetrahydrofuran and its alkyl congeners, presumably via a cleavage reaction. In contrast, the sodium and potassium diarylphosphides do not exhibit this deleterious tendency to any appreciable extent. Thus when forming alkali metal diarylphosphide or employing an alkali metal diarylphosphide as a reactant in an ether reaction medium, especially in the particularly preferred tetrahydrofuran and alkyl-substituted tetrahydrofuran media, it is important to form or use (as the case may be) sodium diarylphosphide or potassium diarylphosphide, or a mixture of the two, rather than a lithium diarylphosphide. On the other hand, when forming and conducting the reaction with a lithium diarylphosphide, use of a hydrocarbon reaction medium, especially an alkylaromatic hydrocarbon reaction medium, is recommended.

Reactions of step b) constitute, inter alia, subject matter of commonly-owned U.S. application Ser. No. 08/639,497, filed Apr. 29, 1996 by K. P. A. Senaratne, all disclosure of said application being incorporated herein by reference.

Another embodiment of this invention is a process of preparing at least one cycloalkyldiarylphosphine by forming a mixture comprising as components or ingredients added or formed in situ (i) at least one potassium diarylphosphide such as potassium diphenylphosphide (ii) sodium, and optionally also sodium hydride, and (iii) at least one cycloalkyl mesylate or tosylate, such as neomenthyl mesylate or tosylate, and maintaining such mixture under conditions, and/or subjecting such mixture to conditions, effective to form at least one cycloalkyldiarylphosphine, such as neomenthyldiphenylphosphine, such conditions including maintaining the reaction mixture under atmosphere containing hydrogen (preferably a hydrogen atmosphere) and/or otherwise exposing the reaction mixture to an atmosphere containing hydrogen (preferably a hydrogen atmosphere). The temperatures, solvents or diluents, and other reaction conditions suitable for the conduct of this embodiment are as described hereinabove.

The following Examples of the practice of this invention are presented for purposes of illustration and not limitation.

EXAMPLE 1

Part A: Preparation of Alkali Metal Diphenylphosphide

A 2-liter autoclave was fitted with a 3.25" diameter high-shear star impeller, a 1-liter hydrogen surge tank, and an alkali metal alloy head tank. The reactor was charged with 500 g of tetrahydrofuran (THF) and 29.5 g of sodium-potassium alloy ($NaK_2$). The mixture was pressured and purged 7 times with hydrogen. The hydrogen pressure was set at 30 psig and the mixture was heated to 40° C. while stirring at 1750 rpm. No evidence of hydrogen uptake was observed. A 44.4 wt % solution formed from 200 g of triphenylphosphine (TPP) and 250 g of THF was fed to the reactor over a 1.5-hour period. At the start, hydrogen uptake was rapid but slowed considerably towards the end of the feed. After several hours the reactor was sampled and found that a conversion of only 85–90% had occurred. An additional 4.5 grams of $NaK_2$ was blown into the reactor under nitrogen pressure. The reactor was again purged with hydrogen and left to react. Again conversion was not complete and an additional 3.15 g of $NaK_2$ was fed to the reactor. This completely converted the TPP to alkali metal diphenylphosphide.

Part B: Preparation of Neomenthyldiphenylphosphine (NMDPP)

Over a 45-minute period, a solution of menthyl mesylate (220 g) in 108 g of THF was pumped into the reactor containing the reaction mixture formed in Part A above. The reactor temperature was maintained at 30°–40° C. for 24 hours before quenching the reaction mixture with water (400 g). An 81% yield of 99.8 wt % NMDPP was obtained upon collecting and stripping the organic phase and crystallizing the product from methanol.

EXAMPLE 2

Part A: Preparation of Alkali Metal Diphenylphosphide

The 2-liter autoclave, equipped as in Example 1, was charged with 390 g of THF and 31.3 g of NaK$_2$ alloy. The mixture was pressured and purged 7 times with hydrogen. The hydrogen pressure was set at 30 psig and the mixture was heated to 40° C. while stirring at 710 rpm. No evidence of hydrogen uptake was observed. A 30 wt % solution formed from 169 g of TPP and 394 g of THF was fed to the reactor over a 4.75-hour period. At the start of the feed the hydrogen uptake was slow but steady. At the end of the feed the reactor was sampled and it was found that the conversion was 98% and that the product was very pure. The mixture was left to stand overnight (2:30 am to 8:00 am) at 40° C. under 50 psig hydrogen. All but a trace of the TPP was converted to alkali metal diphenylphosphide.

Part B: Preparation of Neomenthyldiphenylphosphine (NMDPP)

An unfiltered solution of menthyl mesylate (181 g) in 261 g THF, which solution contained suspended particulate matter, was blown all at once into the reactor containing the reaction product mixture formed in Part A hereof. The temperature rose from 40° C. to 55° C. The reaction temperature was maintained at 50° C. for 5 hours. Conversion was greater than 95 %. The reaction was then quenched with 400 g of water. A 79 % yield of 99.8 wt % NMDPP was obtained upon collecting and stripping the organic phase and crystallizing the product from methanol.

EXAMPLE 3

Preparation of Alkali Metal Diphenylphosphide

A 300 mL 316SS autoclave was fitted with 1/16" OD drip tip connected to a NaK$_2$ head tank charged with 6.52 g (0.193 g mole atoms) of NaK$_2$ alloy and pressured to 30 psig with nitrogen. The reactor was charged with 38.17 g (0.145 mole) of TPP and 127.6 g of THF. The reactor was fitted with a 1-liter hydrogen surge tank and then purged 5 times with 30 psig H$_2$. The reactor was pressured to 29 psig H$_2$ heated to 40° C. and then charged with an aliquot of NaK$_2$. The temperature kicked to 44° C. and then decreased. Ten more charges of NaK$_2$ were made over the next 100 minutes. With each addition the temperature jumped 1–2 degrees C. The reactor was sampled 2.5 hours after the initial addition, and the reaction mixture was found to be >95 % converted. The ratio of diphenylphosphide to the analogous phospholane in the product mixture was 14.0:1. The reactor was pressured to 50 psig H$_2$ and left to react at 40° C. for 12 additional hours. At the end of that period the pressure had dropped 10 psig to 40 psig. Analysis revealed that TPP was still present but the conversion was >99%. The ratio of DPP to phospholane was 12.2:1. Based on GC wt % the yield of DPP was 72%.

Some of the advantages of conducting the process with feed of triarylphosphine to the alkali metal alloy in the presence of excess hydrogen will be apparent from a comparison of Examples 1 and 2 with Example 3.

EXAMPLE 4

Part A: Preparation of Alkali Metal Diphenylphosphide

A 3500 gallon carbon steel autoclave equipped with a high-shear dispersion impeller was charged with 754 gallons of anhydrous tetrahydrofuran (THF) and 198 lbs of NaK$_2$. The reactor was pressured to 30 psig hydrogen and vented three times. The hydrogen pressure was set at 30 psig. Agitation was set at 155 RPM which corresponds to an impeller tip speed of 29 feet/second. A 23 wt % solution formed from 1100 lbs of triphenylphosphine (TPP) and 3678 lbs of THF was fed to the reactor over a period of 9.5 hrs. Throughout the TPP feed the reactor pressure was maintained at 30 psig via subsurface hydrogen feed directed under the reactor impeller. During the feed the reaction temperature rose from 32° C. to 42° C. Agitation was continued for 1.5 hours after completion of the TPP feed before venting hydrogen. The reactor was then sampled. $^{31}$P NMR analysis of the sample showed that it contained 99.6 mole % of potassium diphenylphosphide and only 0.41 mole % of other phosphorus species.

Part B: Preparation of Neomenthyldiphenylphosphine (NMDPP)

The autoclave was charged with 2510 lbs of a 48% solution of menthyl mesylate in THF and then pressured to 30 psig with hydrogen. The mixture was allowed to react for 4 hours at 50°–55° C. The reactor was vented and sampled. $^{31}$P NMR analysis of the sample showed that it contained 94.8 mole % neomenthyldiphenylphosphine.

When reactions analogous to those of Part A of Example 4 were conducted in similar manner and scale except that NaK$_2$ was fed to a solution of TPP in THF under a nitrogen atmosphere, maximum yield of potassium diphenylphosphide was less than 60%.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended, formed in situ, or mixed with one or more other substances, components and/or ingredients in accordance with the present disclosure. Thus the fact that a substance, component or ingredient may have lost its original identity through a chemical reaction or transformation during the course of contacting, blending, formation in situ, or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process of preparing at least one alkali metal diarylphosphide which comprises mixing together at least one triarylphosphine optionally dissolved in an anhydrous organic liquid solvent, and a two-phase mixture of at least one alkali metal in an anhydrous organic liquid diluent, in the presence of molecular hydrogen and under conditions effective to produce at least one alkali metal diarylphosphide.

2. A process according to claim 1 wherein said alkali metal is potassium or a mixture or alloy of potassium with at least one other alkali metal.

3. A process according to claim 1 wherein said alkali metal is sodium or potassium, or a mixture or alloy of sodium and potassium.

4. A process according to claim 3 wherein said at least one triarylphosphine is already dissolved in an anhydrous organic liquid solvent when mixed with the sodium or potassium, or mixture or alloy of sodium and potassium.

5. A process according to claim 1 wherein said alkali metal is an alloy of sodium and potassium of the empirical formula $NaK_2$.

6. A process of preparing at least one alkali metal diarylphosphide which comprises introducing at least one triarylphosphine into a two-phase mixture of at least one alkali metal in an anhydrous organic liquid diluent, in the presence of molecular hydrogen and under conditions effective to produce at least one alkali metal diarylphosphide.

7. A process according to claim 6 wherein said alkali metal is potassium or a mixture or alloy of potassium with at least one other alkali metal.

8. A process according to claim 6 wherein said alkali metal is sodium or potassium, or a mixture or alloy of sodium and potassium.

9. A process according to claim 6 wherein said alkali metal is an alloy of sodium and potassium of the empirical formula $NaK_2$.

10. A process according to claim 6 wherein said triarylphosphine is a triarylphosphine in which each aryl group has, independently, from 6 to 10 carbon atoms and contains only aromatic unsaturation.

11. A process according to claim 6 wherein said triarylphosphine is triphenylphosphine.

12. A process according to claim 6 wherein said alkali metal is sodium or potassium, or a mixture or alloy of sodium and potassium; and wherein said triarylphosphine is a triarylphosphine in which each aryl group has, independently, from 6 to 10 carbon atoms and contains only aromatic unsaturation.

13. A process according to claim 6 wherein said alkali metal is a mixture or alloy of sodium and potassium; and wherein said triarylphosphine is triphenylphosphine.

14. A process of preparing at least one alkali metal diarylphosphide which comprises introducing triarylphosphine into a dispersion or slurry of at least one alkali metal in an anhydrous organic liquid diluent under a pressurized atmosphere of molecular hydrogen such that at least one alkali metal diarylphosphide is formed in solution.

15. A process according to claim 14 wherein said alkali metal is sodium or potassium, or a mixture or alloy of sodium and potassium; wherein said triarylphosphine is a triarylphosphine in which each aryl group has, independently, from 6 to about 10 carbon atoms and contains only aromatic unsaturation; and wherein the process is performed such that at least about 95% conversion of said triarylphosphine occurs.

16. A process according to claim 15 wherein said alkali metal is a mixture or alloy of sodium and potassium; and wherein said triarylphosphine is triphenylphosphine.

17. A process according to claim 14 wherein the triarylphosphine is introduced as a solution.

18. A process according to claim 17 wherein said solution is formed from said triarylphosphine and (i) tetrahydrofuran or (ii) at least one liquid alkyl-substituted tetrahydrofuran, or a mixture of (i) and (ii).

19. A process according to claim 14 wherein said organic liquid diluent is (i) tetrahydrofuran or (ii) at least one liquid alkyl-substituted tetrahydrofuran, or (iii) a mixture of (i) and (ii).

20. A process according to claim 19 wherein the triarylphosphine is introduced as a solution formed from said triarylphosphine and (i) tetrahydrofuran or (ii) at least one liquid alkyl-substituted tetrahydrofuran, or (iii) a mixture of (i) and (ii).

21. A process according to claim 20 wherein said alkali metal is a mixture or alloy of sodium and potassium; and wherein said triarylphosphine is triphenylphosphine.

22. A process according to claim 15 wherein the triarylphosphine is introduced as a solution.

23. A process according to claim 22 wherein said solution is formed from said triarylphosphine and (i) tetrahydrofuran or (ii) at least one liquid alkyl-substituted tetrahydrofuran, or a mixture of (i) and (ii).

24. A process according to claim 23 wherein the organic liquid diluent of said dispersion or slurry is (i) tetrahydrofuran or (ii) at least one liquid alkyl-substituted tetrahydrofuran, or (iii) a mixture of (i) and (ii).

25. A process according to claim 24 wherein the solvent of said solution and the organic liquid diluent of said dispersion or slurry are the same respective substances.

* * * * *